(12) United States Patent
Best et al.

(10) Patent No.: US 7,355,040 B2
(45) Date of Patent: Apr. 8, 2008

(54) PROCESS FOR THE PREPARATION OF CEPHALOSPORIN COMPOUNDS AND SYNTHETIC INTERMEDIATES

(76) Inventors: Desmond John Best, Pfizer Global Research and Development. Ramsgate Road, Sandwich, Kent, CT13 9NJ (GB); George Burton, SmithKline Beecham Pharmaceuticals R & D, 1250, South Collegeville, PA (US) 19426-0989; Brian Charles Gasson, Pfizer Global Research and Development, Ramsgate Road, Sandwich, Kent, CT13 9NJ (GB); Neal Frederick Osborne, Pfizer Global Research and Development, Ramsgate Road, Sandwich, Kent, CT13 9NJ (GB); Graham Walker, Pfizer Global Research and Development, Ramsgate Road, Sandwich, Kent, CT13 9NJ (GB)

(*) Notice: Subject to any disclaimer, the term of this patent is extended or adjusted under 35 U.S.C. 154(b) by 450 days.

(21) Appl. No.: 10/994,983

(22) Filed: Nov. 22, 2004

(65) Prior Publication Data

US 2005/0165229 A1    Jul. 28, 2005

Related U.S. Application Data

(62) Division of application No. 09/918,152, filed on Jul. 30, 2001, now Pat. No. 6,825,344.

(30) Foreign Application Priority Data

Aug. 3, 2000    (GB) .................................. 0019124.7

(51) Int. Cl.
*C07D 501/20* (2006.01)
*C07D 505/18* (2006.01)
*C07D 471/04* (2006.01)

(52) U.S. Cl. ...................... 540/205; 540/301; 540/222; 540/228; 540/230

(58) Field of Classification Search ................. 540/205, 540/301, 222, 228, 230
See application file for complete search history.

(56) References Cited

U.S. PATENT DOCUMENTS

| 5,464,826 | A |  | 11/1995 | Grindey et al. |
| 5,688,925 | A |  | 11/1997 | Allevi et al. |
| 6,825,344 | B2 | * | 11/2004 | Best et al. .................. 540/205 |

FOREIGN PATENT DOCUMENTS

| DE | 25 55 182 |  | 6/1976 |
| DE | 35 16 777 |  | 11/1985 |
| WO | 92/01696 |  | 2/1992 |
| WO | WO 9201696 A | * | 2/1992 |
| WO | 93/25551 |  | 12/1993 |
| WO | WO 9325551 A1 | * | 12/1993 |
| WO | 94/00457 |  | 1/1994 |
| WO | 96/17847 |  | 6/1996 |
| WO | WO 9617847 A1 | * | 6/1996 |

OTHER PUBLICATIONS

Valcavi, Gazz. Chem Italicana 110, 519 (1980).*
Elliott, et al.; Cycloadditions of Cephalosporins; J. Org. Chem. 62:4998-5016 (1997).*
Smith, Organic Synthesis, (McGraw Hill, 1994) pp. 629-630, 638.*
Hawley's Condensed Chemical Dictionary 1th edition pp. 21-22.*
Elliott et al., "Cycloadditions of Cephalosporins. A Comprehensive Study of the Reaction of Cephalosporin Triflates with Olefins, Acetylenes, and Dienes to Form [2+2] and [4+2] Adducts", J. Org. Chem., vol. 62, 1997, pp. 4998-5016.
Chemical Abstracts, vol. 115, 114205u, 1991 (Tanaka et al.).

(Continued)

*Primary Examiner*—Mark L. Berch
(74) *Attorney, Agent, or Firm*—Mary J. Hosley; John H. Engelmann

(57) ABSTRACT

There is provided a process for the preparation of a compound according to Formula (II):

which includes the step of cyclizing a compound of Formula (III):

wherein $R^1$, $R^2$, $R^3$, $R^4$, X and m have meanings which are given in the description.

20 Claims, No Drawings

OTHER PUBLICATIONS

Chemical Abstracts, vol. 114, 185088y, 1991 (Tanaka et al.).
Roush et al., "Diastereo- and Enantioselective Aldehyde Addition Reactions of 2-Allyl-1,3,2-dioxaborolane-4,5-dicarboxylic Esters, a Useful Class of Tartrate Ester Modified Allylboronates", J. Am. Chem. Soc., vol. 107, No. 26, 1985, pp. 8186-8190.
Tanaka et al., "A Facile Access to 3-Formyl-3-cephems Through Oxygen or Air Oxidation of 3-Iodomethyl-3-cephems", Synlett Letters, pp. 660-662, 1990.

Hawley's Condensed Chemical Dictionary 11th Edition, pp. 21-22, 1984.
Valcavi et al., "Some Novel C(3)-Substituted Cephalothin Derivatives", Gazzetta Chimica Italiano, vol. 110, 1980, pp. 519-522.
Smith, Organic Synthesis (McGraw Hill, 1994), pp. 629-630, 638.
Streitwieser, Introduction to Organic Chemistry 4th Edition (Macmillan, 1992), pp. 451-452.
European Search Report, EP 01306325.0, dated Dec. 20, 2001.

* cited by examiner

PROCESS FOR THE PREPARATION OF CEPHALOSPORIN COMPOUNDS AND SYNTHETIC INTERMEDIATES

CROSS-REFERENCE TO RELATED APPLICATIONS

This is a divisional of Ser. No. 09/918,152, now U.S. Pat. No. 6,825,344 filed on Jul. 30, 2001, which claims priority to Great Britain Application No. 0019124, filed Aug. 3, 2000.

This invention relates to a process for the preparation of cephalosporin compounds and intermediates for the synthesis of such compounds.

WO 92/01696 discloses compounds of formula (I):

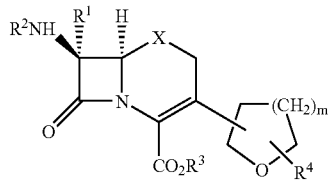

(I)

wherein $R^1$ is hydrogen, methoxy or formamido;

$R^2$ is an acyl group, in particular that of an antibacterially active cephalosporin;

$CO_2R^3$ is a carboxy group or a carboxylate anion, or $R^3$ is a readily removable carboxy protecting group (such as a pharmaceutically acceptable in vivo hydrolysable ester group); $R^4$ represents hydrogen or up to four substituents selected from alkyl, alkenyl, alkynyl, alkoxy, hydroxy, halogen, amino, alkylamino, acylamino, dialkylamino, $CO_2R$, $CONR_2$, $SO_2NR_2$ (where R is hydrogen or $C_{1-6}$ alkyl), aryl and heterocyclyl, which may be the same or different and wherein any $R^4$ alkyl substituent is optionally substituted by any other $R^4$ substituent; X is S, SO, $SO_2$, O or $CH_2$; and m is 1 or 2; and salts thereof. Compounds of formula (I) have antibacterial activity.

WO 92/01696 discloses various methods of synthesis of compounds of formula (I). It is an object of the present invention to provide alternative process enabling more convenient methods of synthesis of compounds of formula (I). Other objects and advantages of the present invention will be apparent from the following description.

According to the present invention a process for the preparation of a compound of formula (II) is provided

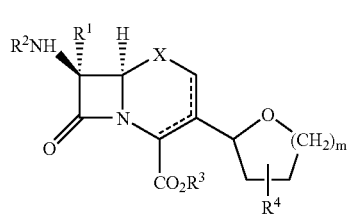

(II)

which process includes the step of cyclising a compound of formula (III):

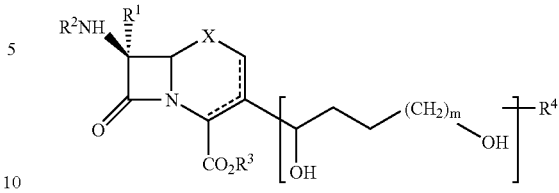

(III)

wherein in formulae (II) and (III) $R^1$, $R^2$, $R^3$, $R^4$, X and m are as defined in formula (I) above and the dotted line indicates that the compounds (II) and (II) may be a 2-cephem or a 3-cephem system, and where in formula (III) the substituent(s) $R^4$ when other than hydrogen may replace any of the hydrogen atoms bonded to carbon atoms in the side chain.

In compounds (II) the bonding carbon atom of the cyclic ether moiety which links the ring to the cephalosporin nucleus is asymmetric. The present invention includes either stereoisomer, as well as mixtures of both isomers.

In compounds of formula (II) wherein $R^1$ is formamido, the formamido group can exist in conformations wherein the hydrogen atoms of the —NH—CHO moiety are cis- or trans-; of these the cis conformation normally predominates.

Preferred compounds within formula (II) are pharmaceutically acceptable, i.e. are compounds of formula (IIA) or pharmaceutically acceptable salts or pharmaceutically acceptable in vivo hydrolysable esters thereof:

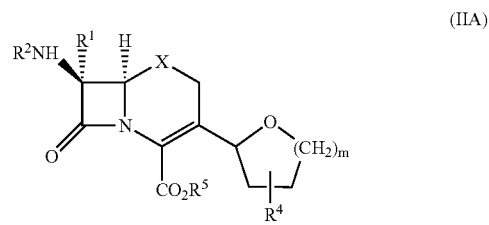

(IIA)

wherein $R^1$, $R^2$, $R^4$, m and X are as defined with respect to formula (II) and the group $CO_2R^5$ is $CO_2R^3$ where $CO_2R^3$ is a carboxy group or a carboxylate anion.

Those compounds of the formula (II) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (IIa) or a pharmaceutically acceptable salt or pharmaceutically acceptable in viva hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

It will be appreciated that also included within the scope of the invention are processes for the preparation of salts and carboxy-protected derivatives, including in vivo hydrolysable esters, of any carboxy groups that may be present as optional substituents in compounds of formula (II) or (IIa). Also included within the scope of the invention are processes for the preparation of acid addition salts of any amino group or substituted amino group that may be present as optional substituents in compounds of formula (II) or (IIa).

Suitable ester-forming carboxyl-protecting groups $R^3$ are those which may be removed under conventional conditions. Such groups include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^7$ where $R^7$ is aryl or heterocyclic, or an in vivo hydrolysable ester radical such as defined below.

When used herein the term 'aryl' includes phenyl and naphthyl, each optionally substituted with up to five, preferably up to three, groups selected from halogen, mercapto, $(C_{1-6})$ alkyl, phenyl, $(C_{1-6})$ alkoxy, hydroxy$(C_{1-6})$alkyl, mercapto$(C_{1-6})$alkyl, halo$(C_{1-6})$alkyl, hydroxy, amino, nitro, carboxy, $(C_{1-6})$ alkylcarbonyloxy, alkoxycarbonyl, formyl, or $(C_{1-6})$alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo$(C_{1-6})$alkyl, hydroxy, carboxy, carboxy salts, carboxy esters such as $(C_{1-6})$alkoxycarbonyl, $(C_{1-6})$alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautomeric forms depending on the nature of the heterocyclyl group; all such tautomeric forms are included within the scope of the invention.

The term 'heteroaryl' as used herein means a heteroaromatic heterocyclic ring or ring system, suitably having 5 or 6 ring atoms in each ring.

When used herein the terms 'ally' alkenyl, alkynyl and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

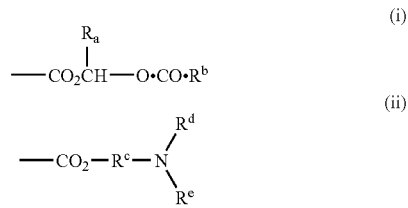

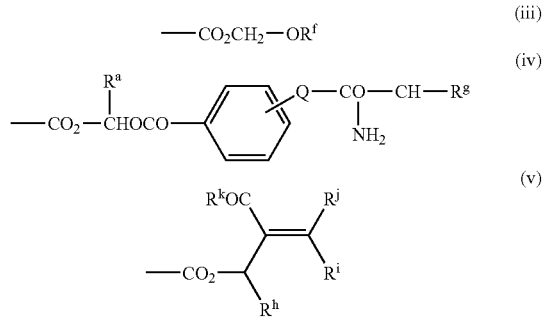

wherein $R^a$ is hydrogen, $(C_{1-6})$ alkyl, $(C_{3-7})$ cycloalkyl, methyl, or phenyl, $R^b$ is $(C_{1-6})$alkyl, $(C_{1-6})$alkoxy, phenyl, benzyl, $(C_{3-7})$ cycloalkyl, $(C_{3-7})$ cycloalkyloxy, $(C_{1-6})$ alkyl $(C_{3-7})$cycloalkyl, 1-amino $(C_{1-6})$alkyl, or 1-$(C_{1-6})$alkyl) amino $(C_{1-6})$ alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$alkoxy; Q is oxygen or NH; $R^h$ is hydrogen or $(C_{1-6})$alkyl; $R^i$ is hydrogen, $(C_{1-6})$alkyl optionally substituted by halogen, $(C_{2-6})$alkenyl, $(C_{1-6})$alkoxycarbonyl, aryl or heteroaryl; or $R^h$ and $R^i$ together form $(C_{1-6})$alkylene; $R^j$ represents hydrogen, $(C_{1-6})$alkyl or $(C_{1-6})$alkoxycarbonyl; and $R^k$ represents $(C_{1-8})$alkyl $(C_{1-8})$alkoxy, $(C_{1-6})$alkoxy$(C_{1-6})$alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl)but-2-enyl; lactone groups such as phthalidyl and dimethoxyphthalidyl; and esters linked to a second β-lactam antibiotic or to β-lactamase inhibitor.

A further suitable pharmaceutically acceptable in vivo hydrolysable ester group is that of the formula:

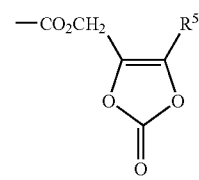

wherein $R^5$ is hydrogen, $C_{1-6}$ alkyl or phenyl.

Suitable pharmaceutically acceptable salts of the carboxy group of the compound of formula (II) include metal salts, eg aluminium, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)-amine, cycloalkylamines such as dicyclohexylamine, or with procaine, dibenzylamine, N,N-dibenzylethylene-diamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In compounds of formula (II), (IIa), and (III) the group X may be sulphur or an oxidised sulphur atom, i.e. a sulphoxide (SO) or sulphone ($SO_2$) group. When X is a sulphoxide group it will be understood that α- and β-isomers may exist; processes for the preparation of both such isomers are encompassed within the scope of the present invention.

Examples of X include S, SO, $SO_2$, O and $CH_2$.

Preferably X is S, O or $CH_2$.

Advantageously $R^1$ is hydrogen.

Suitably, the cyclic ether at the 3-position of the cephalosporin nucleus in formulae (II) and (IIA) is unsubstituted or substituted by up to three substituents, $R^4$, selected from $(C_{1-6})$alkyl, for example methyl, $(C_{1-6})$alkoxy, for example methoxy, $(C_{1-6})$alkoxycarbonyl for example methoxycarbonyl, $(C_{1-6})$alkoxy $(C_{1-6})$alkyl, for example methoxymethyl, and $(C_{1-6})$alkanoyloxy $(C_{1-6})$alkyl, for example acetoxymethyl. Preferably the cyclic ether at the 3-position of the cephalosporin nucleus is unsubstituted.

Preferably m is 1, so that the cyclic ether at the 3-position in formulae (II) and (IIA) is a tetrahydrofuranyl system, in particular an (S)-tetrahydrofuran-2-yl ring system, ie:

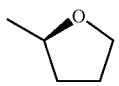

Suitable acyl groups $R^2$ include those of formulae (a)-(f):

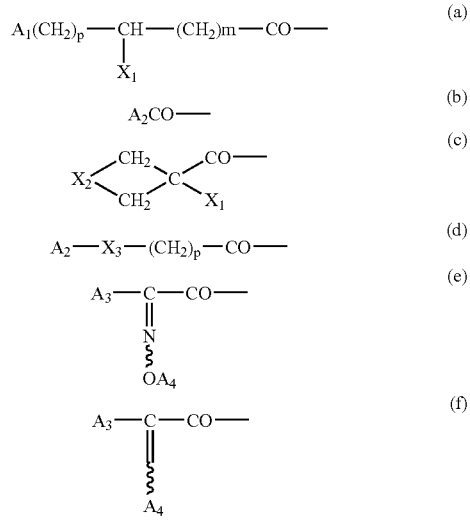

wherein p is 0, 1 or 2; m is 0, 1 or 2; $A_1$ is $(C_{1-6})$ alkyl, substituted $(C_{1-6})$ alkyl, $(C_{3-6})$ cycloalkyl, cyclohexenyl, cyclohexadienyl, an aromatic (including heteroaromatic) group, such as phenyl, substituted phenyl, thienyl, pyridyl, or an optionally substituted thiazolyl group, a $(C_{1-6})$ akylthio group or $(C_{1-6})$ alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group, for example a phenyl, 2,6-dimethoxyphenyl,2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a $-CH_2OCH_2-$, $-CH_2SCH_2-$ or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, $(C_{1-6})$alkyl, $(C_{3-8})$ cycloalkyl, $(C_{3-8})$ cycloalkyl$(C_{1-6})$alkyl, $(C_{1-6})$ alkoxycarbonyl$(C_{1-6})$ alkyl, $(C_{2-6})$ alkenyl, carboxy$(C_{1-6})$alkyl, $(C_{2-6})$ alkynyl, aryl or $(C_{1-6})$alkyl substituted by up to three aryl groups.

Suitably when $R^2$ is a group (a), $A_1$ is $(C_{1-6})$ alkyl, $(C_{3-6})$ cycloalkyl, cyclohexenyl, cyclohexadienyl, phenyl, substituted phenyl such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is O.

Alternatively when $R^2$ is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-amino-1,2,4-thiadiazol-3-yl and 4-aminopyrimid-2-yl.

In compounds of formula (Ia), a particularly preferred group for $A_3$ is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (IIa) or (III) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of formula (IIa) or (III) wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Certain compounds of formula (II), (IIA) or (III) include an amino group which may be protected. Suitable amino protecting groups are those well known in the art which may be removed under conventional conditions without disruption of the remainder of the molecule.

Examples of amino protecting groups include $(C_{1-6})$ alkanoyl; benzoyl; benzyl optionally substituted in the phenyl ring by one or two substituents selected from $(C_{1-4})$ alkyl, $(C_{1-4})$ alkoxy, trifluoromethyl, halogen, or nitro; $(C_{1-4})$ alkoxycarbonyl; benzyloxycarbonyl or trityl substituted as for benzyl above; allyloxycarbonyl, trichloroethoxycarbonyl or chloroacetyl.

Some of the compounds of formula (III) may be crystallised or recrystallised from solvents such as organic solvents. In such cases solvates may be formed. This invention includes within its scope processes in which stoichiometric solvates of compounds of formula (II) including hydrates as well as compounds containing variable amounts of water that may be produced by processes such as lyophilisation, are prepared.

Suitable and preferred configurations and substituents of the compound of formula (III) are as discussed above by analogy with compounds of formula (II). It will be appreciated that the compounds (III) may exist in a number of diastereoisomers, and all of these are encompassed within formula (III). For example when m is 1 the 1,4-dihydroxylbut-1-yl side chain can exist in two diastereoisomers, one of which is more polar than the other. The less polar of these is preferred as it appears to lead to preferential formation of the (S)-tetrahydro furan-2-yl ring system. These isomers may be separated by conventional procedures such as chromatography.

The cyclisation reaction of the process of the invention may suitably be carried out by treatment of the compounds (III) with an acid catalyst, for example an inorganic acid such as hydrochloric acid or an organic acid, such as an organic sulphonic acid such as an arylsulphonic acid, eg toluene-4-sulphonic acid. Alternatively the cyclisation reaction may be carried out by treatment of the compounds (III) with an acylating agent, such as an acid anhydride, for example trifluoromethane sulphonic anhydride, in the presence of a base such as triethylamine or lutidine. Compounds (III) exist as two diastereoisomers, and these may be cyclised stereospecifically by the use of an acylating agent as described above. The reaction may be suitably carried out in an organic solvent, such as a halogenated hydrocarbon, eg dichloromethane, which is preferably pre-dried. Suitably the reaction is carried out at reduced temperature, eg below 0° C., such as below −20° C., eg at around −70° C. After reaction the mixture may be worked up and the product compound isolated by conventional methods.

Compounds of formula (III) may be prepared from known compounds of formula (IV):

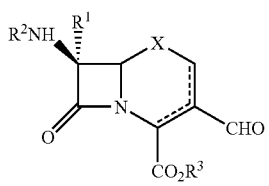
(IV)

where $R^1$, $R^2$, $R^3$ and X are as defined above. Suitably $R^2$ may be an amino-protecting group such as those discussed above, for example phenylacetyl (so that $R^2NH$ is a phenylacetamido group), and $R^3$ may be an ester forming carboxyl-protecting group such as those discussed above, for example diphenylmethyl or p-methoxybenzoyl. Compounds (IV) are disclosed in H. Tanaka et al, Synlett (1990) p 660.

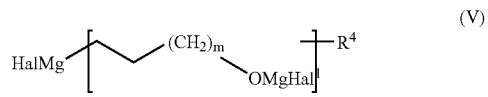
(V)

The reaction between the compound (IV) and Grignard reagent (V) may be carried out in an organic solvent such as an ether, eg THF, preferably at reduced temperature, eg less than 0° C., eg less than −50° C., eg around −70° C., suitably in the presence of lithium chloride, preferably in dry conditions under an inert atmosphere such as argon. After this the reaction mixture may be worked up and the product compound (III) isolated in a conventional manner.

Grignard reagents (V) may themselves be prepared from compounds of formula (VI):

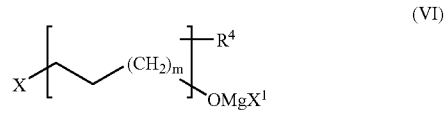
(VI)

where $R^4$ and m are as defined in (V) above, and X and $X^1$ are the same or different halogens, eg X may be chlorine and $X^1$ bromine, by reaction of compounds (VI) with magnesium. This reaction may suitably be carried out in an organic solvent such as THF, in dry conditions, under an inert atmosphere, eg argon.

Compounds (VI) may themselves be prepared by reaction of compounds (VII):

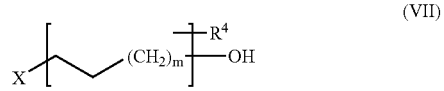
(VII)

where $R^4$ and m are as defined above X is a halogen such as chlorine, with a Grignard reagent $RMgX^1$ where $X^1$ is a halogen such as bromine, and R is an alkyl group such as methyl. This reaction may suitably be carried out in an organic solvent such as THF in dry conditions, under an inert atmosphere, such as argon.

The reaction from compounds (VII) to (V) may be carried out in situ.

In a second way the compound (IV) may first be converted to a compound (VIII):

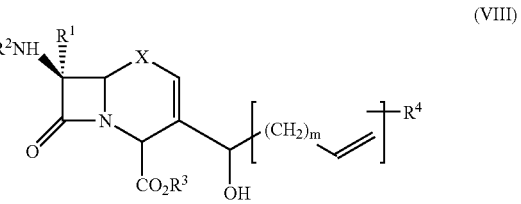
(VIII)

where $R^1$, $R^2$, $R^3$, $R^4$ m and X are as defined with respect to formula (III). Of the two possible configuration of the hydroxyl group in compounds (VIII) ie (VIII A) and (VIII B):

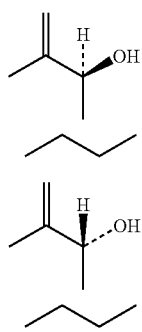

(VIII A)

(VIII B)

(VIII A) is preferred as leading to a preferred configuration of the 3-position cyclic ether ring in formula (II) above. The compound (VIII) may then be hydroxylated to form corresponding compounds (III) having the terminal hydroxyl group. Suitably this may be achieved by treatment of compounds (VIII) with borane-tetrahydrofuran complex, followed by treatment with water or dilute aqueous alkali metal hydroxide solution, and hydrogen peroxide.

Compounds of formula (IV) may be formed into compounds (VIII) by reaction with an organometallic reagent.

In one such method the compound (IV) may be reacted with the Grignard reagent (IX):

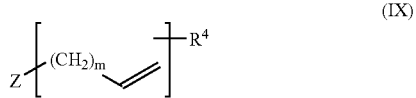

(IX)

where m and $R^4$ are as defined in formula (VIII). Z may be YMg where Y is a halogen such as chlorine or bromine, and the reaction may be carried out in an organic solvent such as THF, suitably at a reduced temperature, eg around −70° C., suitably in the presence of lithium chloride.

Alternatively compounds (VIII) may be prepared stereospecifically from compounds (IV) by the use of compounds (IX) in which Z is a chirally inducing group which leads to preferential formation of a desired configuration of the hydroxyl group in the compound (VIII). A suitable chirally inducing group Z is the boronate group (X):

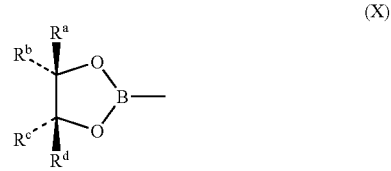

(X)

where $R^a$, $R^b$, $R^c$ and $R^d$ are independently selected from hydrogen, alkyl and protected carboxy, eg $CO_2Re$ where Re is alkyl, for example methyl. For example when $R^a$, $R^b$, $R^c$ and $R^d$ are all alkyl, group (X) may suitably be a pinacol boronate group. Preferably group (X) is a tartrate boronate group wherein $R^a$ is alkylcarboxylate, $R^b$ is hydrogen, $R^c$ is alkylcarboxylate and $R^d$ is hydrogen. Such boronates may be prepared by a known (JACS (1985), 107, 8186-8190) reaction in which known Grignard reagents of formula (IX) in which Z is halogen are reacted with $(CH_3O)_3B$ and a dialkyl tartrate ester.

The reaction between compounds (IV) and boronates (IX) may suitably be carried out in an organic solvent such as toluene at a temperature between −70° C. to +110° C. depending on the nature of the groups $R^a$, $R^b$, $R^c$ and $R^d$.

Compounds (VIII) prepared by this stereospecific route may then be hydroxylated as described above, the stereochemistry of the hydroxyl group shown in (VIII) being preserved in the resultant compounds (III) so formed, and the stereospecific compound (III) may then be stereospecifically cyclised by the use of an acylating agent as described above.

The overall stereospecific route from compounds (IV) to compounds (II) is summarised below:

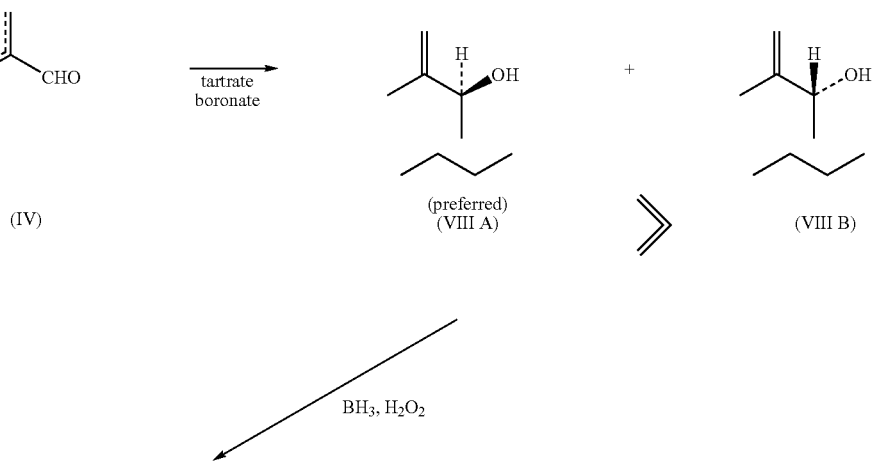

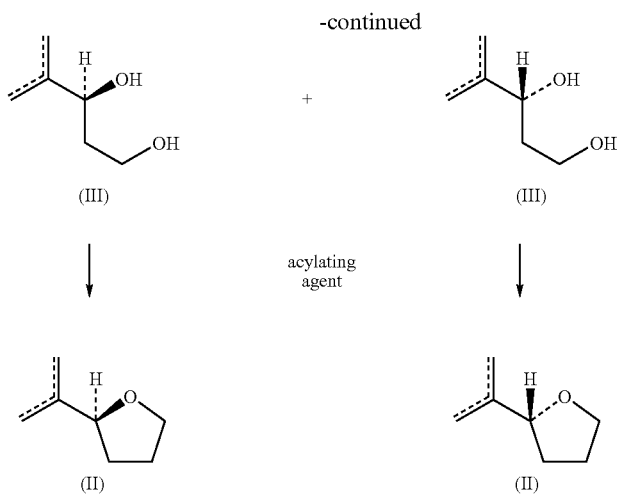

In one embodiment of the process of the invention the compound (IV) is converted into a 2-cephem compound of formula (III), ie of formula (III A):

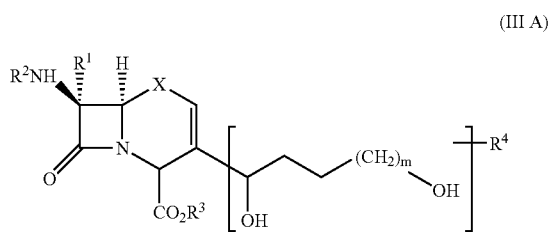

which is converted during the cyclisation process of the invention into a 2-cephem compound of formula (II), ie of formula (II B):

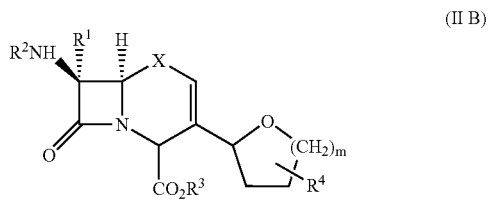

where $R^1$, $R^2$, $R^3$, $R^4$, X and m are as defined in formulae (II) and (III) above. $R^2$ and $R^3$ may be the above-described amino- and carboxy-protecting groups.

The 2-cephem compound (II B) produced by this embodiment may be converted to a 3-cephem compound of formula (II). When X is sulphur conversion of 2-cephems to 3-cephems may be carried out by the generally known method of oxidising the sulphur to form the corresponding 1-oxide, followed by reduction. Oxidation may be performed by using a peroxy acid, for example m-chloroperbenzoic acid. The following reduction process may be carried out using a phosphorus (III) compound, such as phosphorus trichloride in a suitable solvent such as dimethyl formamide or dichloromethane.

When $R^2$ and $R^3$ are respectively amino- and carboxy-protecting groups, these may be removed and replaced by respectively an acyl group of an antibacterially active cephalosporin, and a salt forming cation or pharmaceutically acceptable in-vivo hydrolysable ester group.

An amino-protecting group $R^2$ may be removed from the compound of formula (II) by the known Delft procedure, eg using phosphorus pentachloride in the presence of N-methylmorpholine. The resulting 6-amino compound of formula (II) having $R^2$ as hydrogen may then be converted in an acylation reaction to a compound of formula (II) in which $R^2$ is the acyl group of an antibacterially active cephalosporin by reaction of this amino compound with an N-acylating derivative of an acid of formula $R^2OH$. Suitable reagents and conditions for this acylation reaction are described in WO 92/01696.

A carboxy-protecting group $R^3$ may be removed from the compound of formula (II) by methods which are well known in cephalosporin chemistry. For example a diphenylmethyl or 4-methoxybenzyl protecting group $R^3$ may be removed by reaction with aluminium chloride and anisole in a suitable solvent such as dichloromethane.

Salts and esters of the free acid so formed may be prepared by methods well known in cephalosporin chemistry. For example salts of formula (II) may be formed by reaction with a basic compound of a salt-forming cation, for example aqueous trisodium citrate to form sodium salts. Such a reaction may for example be carried out in aqueous conditions. Esters of formula (II), such as pharmaceutically acceptable in-vivo hydrolysable esters may also be made by methods well known in cephalosporin chemistry. For example esters may be formed by reaction of an alkali metal salt of formula (II) with a compound of formula $R^3X$ where X is a halogen such as iodine and $R^3$ is the ester-forming group, for example acetoxymethyl or pivaloyloxy methyl. Such a reaction may be carried out in an organic solvent such as toluene or N-methylpyrrolidone.

During the course of the reactions described above, mixtures of isomers may be formed. The process of the invention includes the preparation of such isomeric mixtures Isomers produced in the course of these reactions may be separated by conventional techniques such as chromatography.

Certain of the compounds described herein and formed as intermediates in the preparation of compounds of formula (II) are believed to be novel and form a further aspect of this invention, for example compounds of formula (II B), (III), (III A) and (VIII).

Pharmaceutical uses for the compounds of formula (II) are described in WO 92/01696.

The following non-limiting examples illustrate the present invention.

EXAMPLE 1

Diphenylmethyl (4R, 6R, 7R)-3-(1,4-dihydroxybut-1-yl)-7-phenylacetamidoceph-2-em-4-carboxylate Methylmagnesium bromide (3.52 ml of 3M in diethyl ether) was added to a stirred solution of 3-chloropropan-1-ol (1.00 g) in dry tetrahydrofuran (THF) (4 ml) at −20° C. under dry argon. After 15 minutes at −20° C. the mixture was treated with 1,2-dibromoethane (2 drops) and a small portion of the mixture was added to magnesium turnings (382 mg) and dry THF (0.5 ml) at 60° C. under dry argon. After the reaction had initiated the remainder of the mixture was added dropwise over 10 minutes. The mixture was stirred for a further 30 minutes at 60° C., cooled to room temperature, and added, dropwise over 5 minutes, to a stirred solution of diphenylmethyl (4R, 6R, 7R)-3-formyl-7-phenylacetamidoceph-2-em-3-carboxylate (H. Tanaka et al., Synlett, 1990, 660) (676 mg) and oven dried anhydrous lithium chloride (444 mg) in dry THF (10 ml) at −76° C. under dry argon. After 1 hour at −76° C. the mixture was acidified with 5% citric acid and diluted with ethyl acetate (50 ml). The organic layer was separated and washed with brine (10 ml), sat$^d$ NaHCO$_3$ (10 ml), and brine (3×10 ml). The dried (MgSO$_4$) organic layer was evaporated and the residue was chromatographed on silica gel eluting with ethyl acetate/hexane mixtures to give three fractions. The first fraction contained the less polar diastereomer P1 of the title compound which was obtained as an amorphous solid (167 mg), δ ppm [(CD$_3$)$_2$CO] 1.45-1.82 (4H, m), 3.47-3.53 (2H, m), 3.60-3.73 (3H, m), 4.25-4.35 (1H, m), 4.42 (1H, d, J 4.6 Hz), 5.12 (1H, d, J 1.2 Hz), 5.22 (1H, d, 4.0 Hz), 5.56 (1H, dd, J 8.3 and 4.0 Hz), 6.49 (1H, d, J 1.2 Hz), 6.89 (1H, s), 7.21-7.50 (15H, m), 8.07 (1H, d, J 8.3 Hz). The second fraction contained an approximately 2:3 mixture of the diastereomers P1 and P2 of the title compound which was obtained as an amorphous solid (122 mg). The third fraction contained the more polar diastereomer P2 of the title compound which was obtained as an amorphous solid (284 mg), d ppm [(CD$_3$)$_2$CO] 1.30-1.72 (4H, m), 3.48-3.50 (2H, m), 3.60-3.72 (3H, m), 4.13-4.20 (1H, m), 4.29 (1H, d, J 5.2 Hz), 5.17 (1H, d J 3.9 Hz), 5.20 (1H, d, J 1.2 Hz), 5.53 (1H, dd, J 8.3 and 3.9 Hz), 6.44 (1H, br s), 6.86 (1H, s), 7.21-7.48 (15H, m), 8.06 (1H, d, J 8.3 Hz).

EXAMPLE 2

Diphenylmethyl (4R, 6R, 7R)-7-phenylacetamindo-3-[(S)-tetrahydroturan-2-yl]ceph-2-em-4-carboxylate Trifluoromethanesulphonic anhydride (0.14 ml of a solution containing 0.12 ml/ml in dry dichloromethane) was added to a solution of the less polar diastereomer P1 of the diol from Example 1 (40 mg) and triethylamine (28 mg) in dry dichloromethane (1 ml) at −76° C. After 15 minutes at −76° C. the mixture was diluted with ethyl acetate (10 ml) and was washed with 5% citric acid (2 ml), brine (2 ml), sat$^d$ NaHCO$_3$ (2 ml), and brine (3×2 ml). The dried (MgSO$_4$) organic layer was evaporated and the residue was chromatographed on silica gel eluting with ethyl acetate/hexane mixtures to give the title compound as a solid (33 mg), d ppm [(CD$_3$)$_2$CO] 1.52-1.84 (3H, m), 2.01-2.16I(1H+acetone, m), 3.57-3.79 (4H, m), 4.37 (1H, t, J 7.0 Hz), 5.05 (1H, s), 5.21 (1H, d, J 4.0 Hz), 5.56 (1H, dd, J 8.4 and 4.0 Hz), 6.44 (1H, t, J 1.40 Hz), 6.91 (1H, s), 7.21-7.49 (15H, m), 8.05 (1H, d, J 8.4 Hz).

EXAMPLE 3

Diphenylmethyl (4R, 6R, 7R)-7-phenylacetamido-3-[(R)-tetrahydrofuran-2-yl]ceph-2-em-4-carboxylate Treatment of the more polar diastereomer P2 of the diol from Example 1 (40 mg) as for Example 2 gave the title compound as an amorphous solid (31 mg), d ppm [(CD$_3$)$_2$CO] 1.55-1.94 (4H, m), 3.53-3.76 (4H, m), 4.33 (1H, t, J 6.9 Hz), 5.07 (1H, d, J. 1.2 Hz), 5.18 (1H, d, J 3.9 Hz), 5.54 (1H, dd, J 8.9 and 3.9 Hz), 6.47-6.48 (1H, m), 6.87 (1H, s), 7.20-7.49 (15H, m), 8.07 (1H, d, J 8.9 Hz).

EXAMPLE 4

Diphenylmethyl (4R, 6R, 7R)-7-phenylacetamido-3-(tetrahydrofuran-2-yl)ceph-2-em-4-carboxylate a) Toluene-4-sulphonic acid monohydrate (0.2 ml) of a solution containing 5 mg/ml in ethyl acetate) was added to a solution of the less polar diastereomer P1 of the diol from Example 1 (20 mg) in ethyl acetate (1 ml). After 2½ hours at room temperature the mixture was evaporated and the residue chromatographed on silica gel eluting with ethyl acetate/hexane mixtures to give a 2:1 mixture of the (S) and (R)-diastereomers of the title compounds as an amorphous solid (18 mg).
b) Treatment of the more polar diastereomer P2 of the diol from Example 1 (20 mg) as for Example 4(a) (3 hours at room temperature) gave a 2:3 mixture of the (s) and (R)-diastereomers of the title compound as an amorphous solid (19 mg).

EXAMPLE 5

Diphenylmethyl (6R, 7R)-7-phenylacetamido-3-[(S)-tetrahydrofuran-2-yl]ceph-3-em-4-carboxylate-1-oxide The ceph-2-em from Example 2 (59 mg) was dissolved in dichloromethane (2 ml), cooled in an ice bath, and treated with a solution of m-chloroperbenzoic acid (22 mg of 85%) in dichloromethane (0.5 ml). After 15 minutes at ice bath temperature the mixture was treated with m-chloroperbenzoic acid (2 mg). After a further 15 minutes at ice bath temperature the mixture was diluted with ethyl acetate (10 ml) and was washed with sat$^d$ NaHCO$_3$ (2 ml), and brine (3×2 ml). The dried (MgSO$_4$) organic layer was evaporated and the residue was chromatographed on silica gel eluting with ethyl acetate/hexane mixtures to give the title compound as a solid (55 mg), d ppm (CDCl$_3$) 1.40-1.92 (3H, m), 2.24-2.37 (1H, m), 3.23 (1H, dd, J 19.1 and 1.4 Hz), 3.59-3.90 (5H, m), 4.43 (1H, dd, J 4.7 and 1.4 Hz), 4.97 (1H, dd, J 9.0 and 6.7 Hz), 6.08 (1H, dd, J 10.0 and 4.7 Hz), 6.72 (1H, d, J 10.0 Hz), 6.87 (1H, s), 7.26-7.41 (15H, m).

EXAMPLE 6

Diphenylmethyl (6R, 7R)-7-phenylacetamido-3-[(S)-tetrahydrofuran-2-yl]ceph-3-em-4-carboxylate Phosphorus trichloride (0.1 ml of a solution containing 0.17 ml/ml in dry dichloromethane) was added to a stirred, ice bath cooled, mixture of the sulphoxide from Example 5 (55 mg) and dry dimethylformamide (0.05 ml) in dry dichloromethane (2 ml). After stirring for 15 minutes at ice bath temperature the mixture was diluted with ethyl acetate (10 ml) and was washed with sat$^d$ NaHCO$_3$ (2 ml), and brine (3×2 ml). The dried (MgSO$_4$) organic layer was evaporated and the residue was chromatographed on silica gel eluting with ethyl acetate/hexane mixtures to give the title compound as an amorphous solid (45 mg), d ppm (CDCl$_3$) 1.42-1.58 (1H, m), 1.79-1.95 (2H, m), 2.21-2.33 (1H, m), 3.24 (1H, d, J 18.7 Hz), 3.56-3.66 (3H, m), 3.71-3.92 (2H, m), 4.84 (1H, dd, J 9.2 and 6.6 Hz), 4.95 (1H, d, J 4.8 Hz), 5.85 (1H, dd, J 9.1 and 4.8 Hz), 6.04 (1H, d, J 9.1 Hz), 6.86 (1H, s), 7.25-7.42 (15H, m).

EXAMPLE 7

Sodium (6R, 7R)-7-phenylacetamido-3[(S)-tetrahydrofuran-2-yl]ceph-3-em-4-carboxylate A solution of the cephem ester from Example 6 (45 mg) in dry dichloromethane (1 ml) was added to a stirred solution of aluminium chloride (27 mg) in a mixture of anisole (1.5 ml) and dry dichloromethane (0.5 ml) at −40° C. After 15 minutes at −40° C. the cooling bath was removed and the mixture was treated with trisodium citrate (3.5 ml of a 0.5M aqueous solution). After stirring for a further 15 minutes the mixture was diluted with water (10 ml) and dichloromethane (5 ml). The aqueous layer was separated and the organic layer was re-extracted with water (5 ml). The combined aqueous layers were washed with dichloromethane, evaporated to low volume, and chromatographed on HP20 SS eluting with THF/water mixtures. The appropriate fractions were combined, concentrated, and freeze dried to give the title compound as an amorphous solid (26 mg), d ppm (D20) 1.66-2.01 (3H, m), 2.12-2.22 (1H, m), 3.28 and 3.46 (2H, ABq, J 17.7 Hz), 3.61 and 3.69 (2H, ABq, J 14.8 Hz), 3.74-3.92 (2H, m), 4.67-4.73 (1H, m), 5.07 (1H, d, J 4.6 Hz), 5.57 (1H, d, J 4.6 Hz), 7.29-7.40 (5H, m).

EXAMPLE 8

4-Methoxybenzyl (4R, 6R, 7R)-3-(1,4-dihydroxybut-1-yl)-7-phenylacetamidoceph-2-em-4-carboxylate The two isomers of the title compound were prepared as in Example 1 using 4-methoxybenzyl (4R, 6R, 7R)-3-formyl-7-phenylacetamidoceph-2-em-3-carboxylate. Eluted first was the less polar isomer (isomer a, 194 mg), n$_{max}$ (CHCl$_3$) 3415, 1773, 1741 and 1679 cm$^{-1}$, d [(CD$_3$)$_2$CO] 1.48-1.75 (4H, m), 3.48-3.57 (2H, m), 3.66 (2H, s), 3.80 (3H, s), 4.23-4.42 (1H, m), 4.98 (1H, d, J 1.28 Hz), 5.14 (2H, s), 5.26 (1H, d, J 3.94 Hz), 5.53 (1H, dd, J 3.97 and 8.35 Hz), 6.45 (1H, d, J 1.26 Hz), 6.86-6.96 (2H, m), 7.21-7.39 (7H, m), 8.06 (1H, d, J 8.28 Hz). Eluted next was the more polar isomer (isomer b, 160 mg), n$_{max}$ (CHCl$_3$), 3415, 1774, 1740 and 1679 cm$^{-1}$. d [(CD$_3$)$_2$CO] 1.43-1.72 (4H, m), 3.51-3.57 (2H, m), 3.66 (2H, s), 3.80 (3H, s), 4.14-4.22 (1H, m), 5.02 (1H, d, 1.32 Hz), 5.08 (1H, d, J 11.97 Hz), 5.14 (1H, d, J 11.99 Hz), 5.19 (1H, d, J 3.96 Hz), 5.53 (1H, dd, J 3.95 and 8.30 Hz), 6.41 (1H, s), 6.90-6.95 (2H, m), 7.20-7.39 (7H, m), 8.05 (1H, d, J 8.30 Hz).

EXAMPLE 9

4-Methoxybenzyl (4R, 6R, 7R)-7-phenylacetamido-3-[(S)-tetrahydrofuran-2-yl]ceph-2-em-4-carboxylate A solution of isomer a from Example 8 (194 mg) and 2,6-lutidine (0.170 ml) in dry dichloromethane (5 ml) was cooled to −78° C. and treated with trifluoromethanesulphonic anhydride. After 15 minutes a further portion of trifluoromethanesulphonic anhydride (0.04 ml) was added. After a further 15 minutes the solution was diluted with dichloromethane and washed successively with citric acid solution, water, sodium bicarbonate solution, water and brine. The solution was dried over magnesium sulphate and evaporated. The product (159 mg) was isolated by column chromatography of the residue (silica gel, 1:1 hexane:ethyl acetate as eluant). n$_{max}$ (CHCl$_3$) 3414, 1775, 1741 and 1681 cm$^{-1}$. d [(CD$_3$)$_2$CO] 1.52-2.16 (4H, m), 3.60-3.83 (2H, m), 3.65 (2H, s), 3.80 (3H, s), 4.39 (1H, t, J 7.01 Hz), 4.90 (1H, s), 5.10-5.21 (2H, m), 5.21 (1H, d, J 3.89 Hz), 5.55 (1H, dd, J 3.94 and 8.34 Hz), 6.40 (1H, s), 6.94 (2H, d, J 8.67 Hz), 7.21-7.39 (7H, m), 8.04 (1H, d, J 8.34 Hz).

EXAMPLE 10

4-Methoxybenzyl (4R, 6R, 7R)-7-phenylacetamindo-3-[(R)-tetrahydrofuran-2-yl]ceph-2-em-4-carboxylate A solution of isomer b from Example 8 (160 mg) and 2,6-lutidine (0.140 ml) in dry dichloromethane (5 ml) was cooled to −78° C. and trifluoromethanesulphonic anhydride (0.10 ml) was added. After sting at the same temperature for 15 minutes the mixture was diluted with dichloromethane and washed successively with citric acid solution, water, sodium bicarbonate solution, water and brine. The solution was dried over magnesium sulphate and evaporated. The product (70 mg) was obtained by column chromatography of the residue using gradient elution (silica gel; 3:1 going to 1:1 hexane:ethyl acetate). n$_{max}$ (CHCl$_3$) 3414, 1775, 1740 and 1681 cm$^{-1}$. d [(CD$_3$)$_2$CO] 1.58-2.09 (4H, m), 3.57-3.77 (4H, m), 3.80 (3H, s), 4.35 (1H, t, J 7.06 Hz), 4.92 (1H, d, J 1.48 Hz), 5.08 (1H, d, J 11.94 Hz), 5.15 (1H, d, J 11.83 Hz), 5.53 (1H, dd, J 3.93 and 8.32 Hz), 6.44 (1H, d, J 1.40 Hz), 6.90-6.96 (2H, m), 7.20-7.39 (7H, m), 8.05 (1H, d).

EXAMPLE 11

4-Methoxybenzyl (6R, 7R)-7-phenylacetamido-3-[(R)-tetrahydrofuran-2-yl]ceph-3-em-4-carboxylate A solution of 4-methoxybenzyl (4R, 6R, 7R)-7-phenylacetamido-3-[(R)-tetrahydrofuran-2-yl]ceph-3-em-4-carboxylate (70 mg) in dichloromethane (5 ml) was cooled in an ice bath and a solution of m-chloroperbenzoic acid (30 mg) in dichloromethane (1 ml) was added. The mixture was stirred at the same temperature for 35 minutes and then the solution was washed with sodium metabisulphite solution, sodium bicarbonate solution, water and brine. The solution was dried over magnesium sulphate and evaporated. The residue was stirred in dichloromethane (5 ml) and the mixture cooled in an ice bath. Dimethylacetamide (0.037 ml) was added followed by phosphorus trichloride (0.023 ml). The mixture was stirred at 0° C. for 15 minutes and then partitioned between chloroform and sodium bicarbonate solution. The organic phase was washed with water and brine, dried over magnesium sulphate and evaporated. The title compound (25 mg) was isolated by column chromatography of the residue (silica gel, 1:1 hexane:ethyl acetate as eluant). d (CDCl$_3$) 1.51-2.05 (4H, m), 3.32 (1H, d, J 17.15 Hz), 3.49 (1H, d, J 17.75 Hz), 3.60 (1H, d, J 16.18 Hz), 3.69 (1H, d, J 16.26 Hz), 3.74-3.90 (2H, m), 3.80 (3H, s), 4.91 (1H, d, J 4.74 Hz), 5.09 (1H, t, J 7.32 Hz), 5.18 (2H, s), 5.73 (1H, dd, J 4.70 and 9.04 Hz), 6.04 (1H, d, J 9.03 Hz), 6.86-6.89 (2H, m), 7.25-7.40 (7H, m).

EXAMPLE 12

Diphenylmethyl (4R, 6R, 7R)-3-(1-hydroxybut-3-en-1-yl)-7-phenylacetamidoceph-2-em-4-carboxylate (a). via the Grignard reagent. Allylmagnesium chloride (2M in diethyl ether, 4.0 ml, 8 mmol) was added to a solution containing diphenylmethyl (4R, 6R, 7R)-3-formyl-7-phenylacetamidoceph-2-em-4-carboxylate (0.5 g, 11.0 mmol) and lithium chloride (0.35 g, 8 mmol) in tetrahydrofuran (5 ml) at −70° C. After 20 minutes at −70° C., hydrochloric acid (1M, 10 ml, 10 mmol) was added. Ethyl acetate was added and the organic layer was separated, washed with brine, dried (MgSO$_4$), and evaporated. The resulting oil was purified by chromatography (20% to 60% ethyl acetate in hexane, silica gel) giving; first the title compound S-diastereomer, 90 mg (17%), d$_H$ (CDCl$_3$) 2.18 (1H, dt, J 15 Hz and 8 Hz), 2.36 (1H, dt, J 17 and 5 Hz), 3.54 (2H, ABq), 4.18 (1H, m), 4.95-5.15 (4H, m), 5.55-5.7 (2H, m), 6.11 (1H, d, J 9 Hz), 6.36 (1H, s), 6.89 (1H, s), 7.3-7.4 (15H, m), and second; the title compound R-diastereomer, 250 mg (45%), d$_H$ (CDCl$_3$) 2.28 (2H, t, J 7 Hz), 3.62 (2H, ABq), 4.15 (1H, t, J 7 Hz), 4.95-5.2 (4H, m), 5.5-5.65 (2H, m), 6.16 (1H, d, J 9 Hz), 6.20 (1H, s), 6.89 (1H, s), 7.3-7.4 (15H, m).

(b). via a pinacol boronate. A mixture of 2-allyl-4,4,5,5-tetramethyl-1,3,2-dioxaborolane (50 mg, 0.3 mmol), diphenylmethyl (4R, 6R, 7R)-3-formyl-7-phenylacetamidoceph-2-em-4-carboxylate (100 mg, 0.2 mmol), 0.4 nm molecular sieves (50 mg), and toluene (2 ml) was heated under reflux for 3 h and then cooled and purified by chromatography as in part a to give the title compound S-diastereomer, 20 mg (18%), and the R-diastereomer, 23 mg (20%).

(c). via a tartrate boronate. A mixture of dimethyl (R,R)-2-allyl-1,3,2-dixoaborolane-4,5-dicarboxylate (0.67M in toluene, 1.8 ml, 1.2 mmol) and 0.4 nm molecular sieves (50 mg) was stirred at 20° C. for 10 minutes and then cooled to −70° C., and then a solution of diphenylmethyl (4R, 6R, 7R)-3-formyl-7-phenylacetamidoceph-2-em-4-carboxylate (100 mg, 0.2 mmol) in tetrahydrofuran (0.5 ml) was added dropwise. After 2 h at −70° C. the mixture was warned to 20° C. and water and ethyl acetate were added. The organic layer was dried (MgSO$_4$) and evaporated and the residue purified by chromatography as in part a to give the title compound S-diastereomer, 45 mg (43%), and the R-diastereomer 8 mg (8%).

EXAMPLE 13

Diphenylmethyl (4R, 6R, 7R)-3-(1,4-dihydroxybut-1-yl)-7-phenylacetamidoceph-2-em-4-carboxylate Borane-tetrahydrofuran complex (1M in tetrahydrofuran, 11.0 ml, 11.0 mmol) was added to diphenylmethyl (4R, 6R, 7R)-3-(1-hydroxybut-3-en-1-yl)-7-phenylacetamidoceph-2-em-4-carboxylate (S-diastereomer, 100 mg, 0.18 mmol) in tetrahydrofuran (2 ml) at 20° C. After 30 minutes water (1 ml) was added and the pH taken to within the range 7 to 8 with dilute aqueous sodium hydroxide. Hydrogen peroxide (30% in water, 0.15 ml, 1.35 mmol) was then added, and the pH maintained at 7 to 8 for 20 minutes, after which water and ethyl acetate were added. The organic layer was washed with brine, dried (MgSO$_4$), and evaporated to give a residue which was purified by chromatography (50 to 100% ethyl acetate in hexane, silica gel) giving the S-diastereomer of the title compound identical to that obtained above (isomer P1), 35 mg (34%).

The invention claimed is:

1. A process for the preparation of a compound of formula (II):

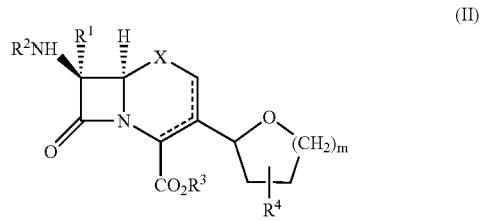

comprising cyclizing a compound of formula (III):

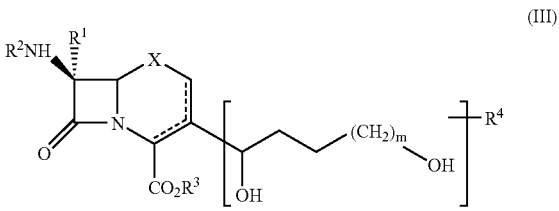

wherein in formulae (II) and (III), R$^1$ is hydrogen, methoxy or formamido;

R$^2$ is an acyl group selected from the group consisting of the following compounds:

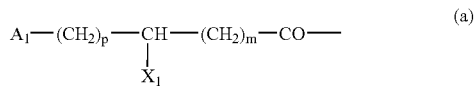

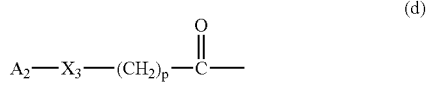

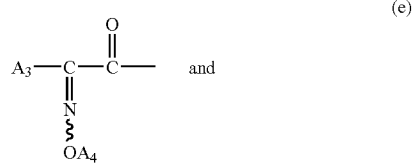

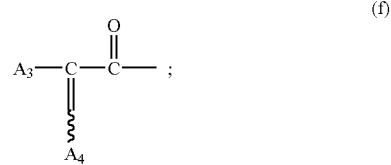

wherein p is 0, 1, or 2; m is 0, 1 or 2; A$_1$ is (C$_{1-6}$) alkyl, substituted (C$_{1-6}$) alkyl, (C$_{3-6}$) cycloalkyl, cyclohexenyl, cyclohexadienyl, an aromatic group, a (C$_{1-6}$) alkylthio group, (C$_{1-6}$) alkyloxy; X$^1$ is a hydrogen or halogen atom, azido, tetrazolyl, hydroxy, acyloxy, amino, uerido, acylamino, heterocyclylamino, guanidino or acylureido group;

$A_2$ is an aromatic group, a phenyl, 2,6-dimethoxyphenyl, 2-alkoxy-1-naphthyl, 3-arylisoxazolyl, or a 3-aryl-5-methylisoxazolyl group, a substituted alkyl group; a substituted dithietane; $X^2$ is a —$CH_2OCH_2$—, —$CH_2SCH_2$— or alkylene group; $X^3$ is an oxygen or sulphur atom; $A_3$ is an aryl or heteroaryl group, phenyl, substituted phenyl, furyl, aminothiazolyl or aminothiadiazolyl in which the amino group is optionally protected; and $A_4$ is hydrogen, $(C_{1-6})$alkyl, $(C_{3-8})$ cycloalkyl, $(C_{3-8})$ cycloalkyl$(C_{1-6})$alkyl, $(C_{1-6})$ alkoxycarbonyl$(C_{1-6})$ alkyl, $(C_{2-6})$ alkenyl, carboxy$(C_{1-6})$ alkyl, $(C_{2-6})$ alkynyl, aryl or $(C_{1-6})$alkyl substituted by up to three aryl groups;

$CO_2R^3$ is a carboxy group or a pharmaceutically acceptable carboxylate salt, or $R^3$ is a readily removable carboxy protecting group selected from the group consisting of benzyl, p-methoxybenzyl, benzoylmethyl, p-nitromethyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, an oxime radical of formula —N=$CHR^7$ where $R^7$ is aryl or heterocyclic, group of formulas (i), (ii), (iii), (iv) and (v):

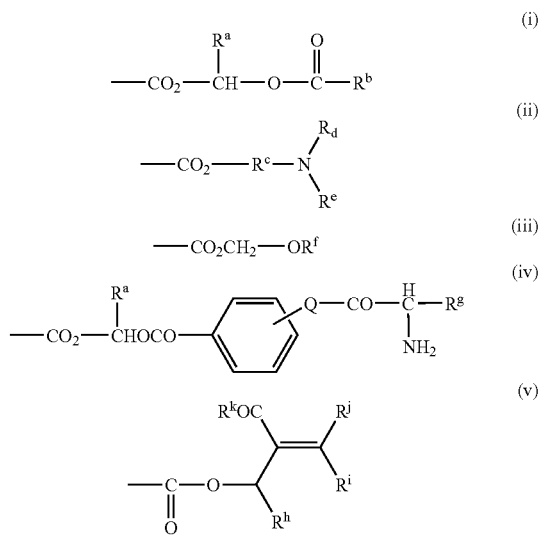

wherein $R^a$ is hydrogen, $(C_{1-6})$ alkyl, $(C_{3-7})$ cycloalkyl, methyl, or phenyl, $R^b$ is $(C_{1-6})$alkyl, $(C_{1-6})$alkyl, $(C_{1-6})$ alkoxy, phenyl, benzyl, $(C_{3-7})$ cycloalkyl, $(C_{3-7})$ cycloalkyloxy, $(C_{1-6})$alkyl $(C_{3-7})$cycloalkyl, 1-amino $(C_{1-6})$alkyl, or 1-(($C_{1-6}$)alkyl) amino $(C_{1-6})$ alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$alkyl; $R^f$ represents $(C_{1-6})$ alkyl, $R^g$ represents hydrogen or phenyl optionally substituted by up to three groups selected from halogen, $(C_{1-6})$ alkyl, or $(C_{1-6})$alkoxy; Q is oxygen or NH; $R^h$ is hydrogen or $(C_{1-6})$alkyl; $R^i$ is hydrogen, $(C_{1-6})$alkyl optionally substituted by halogen, $(C_{2-6})$alkenyl, $(C_{1-6})$alkoxycarbonyl, aryl or heteroaryl; or $R^h$ and $R^i$ together form $(C_{1-6})$alkylene; $R^j$ represents hydrogen, $(C_{1-6})$alkyl or $(C_{1-6})$alkoxycarbonyl; and $R^k$ represents $(C_{1-8})$alkyl, $(C_{1-8})$alkoxy, $(C_{1-6})$alkoxy, $(C_{1-6})$alkoxy$(C_{1-6})$alkoxy or aryl, a group of the formula

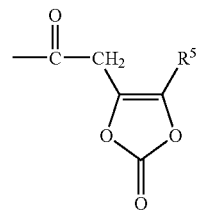

wherein $R^5$ is hydrogen, $C_{1-6}$ alkyl or phenyl; acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; ethoxycarbonyloxymethyl, α-ethoxycarbonyloxyethyl, propoxycarbonyloxyethyl; dialkylaminoalkyl, dimethylaminomethyl, dimethylaminoethyl, diethylaminomethyl or diethylaminoethyl; 2-(isobutoxycarbonyl)pent-2-enyl and 2-(ethoxycarbonyl)but-2-enyl;

$R^4$ represents hydrogen or up to four substituents selected from alkyl, alkenyl, alkynyl, alkoxy, amino, alkylamino, acylamino, dialkylamino, $CO_2R$, $CONR_2$, $SO_2NR_2$ (where R is hydrogen or $C_{1-6}$ alkyl), aryl and heterocyclyl, which may be the same or different and wherein any $R^4$=alkyl substituent is optionally substituted by any other $R^4$ substituent;

X is S, SO, $SO_2$, O, or $CH_2$; and m is 1 or 2; and the dotted line indicates a double bond C2 and C3 or between C3 and C4 of formula II and Formula III, and where in formula (III) the substituent(s) $R^4$ when other than hydrogen may replace any of the hydrogen atoms bonded to carbon atoms in the side chain.

2. A process according to claim 1 wherein the compound of formula (II) is a compound of formula (IIA) or a pharmaceutically acceptable salt or pharmaceutically acceptable in vivo hydrolysable ester thereof:

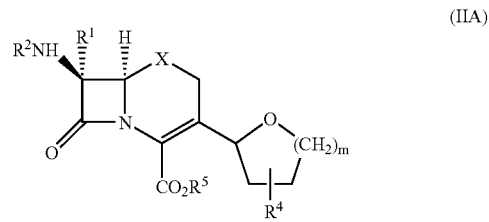

(IIA)

wherein $R^1$, $R^2$, $R^4$, m and X are as defined with respect to formula (II) and the group $CO_2R^5$ is $CO_2R^3$ where $CO_2R^3$ is a carboxy group, or a pharmaceutically acceptable carboxylate salt.

3. A process according to claim 1 or 2 wherein X is S, O, or $CH_2$.

4. A process according to claims 1, 2 or 3 or wherein the cyclic ether at the 3-position of the cephalosporin nucleus in formulae (II) and (IIA) is unsubstituted.

5. A process according to any one of claims 1 to 4 wherein m is 1, so that the cyclic ether at the 3-position in formulae (II) and (IIA) is a tetrahydrofuranyl system.

6. A process according to claim 5 wherein the cyclic ether at the 3-position in formulae (II) and (IIA) is an (S)-tetrahydrofuran-2-yl ring system.

7. A process according to any one of the preceding claims wherein in formula (III) when m is 1 the 1 the 1,4-dihydroxylbut-1-yl side chain is the less polar diastereoisomeric form.

8. A process according to any one of the preceding claims wherein the cyclization reaction of the process of the invention is carried out by treatment of the compounds (III) with an acid catalyst.

9. A process according to claim 1 or 2, wherein the cyclization reaction is carried out by treatment of the compounds (III) with an acylating agent.

10. A process according to claim 1 or 2, wherein the compound of formula (III) is prepared by reacting a compound of formula (IV):

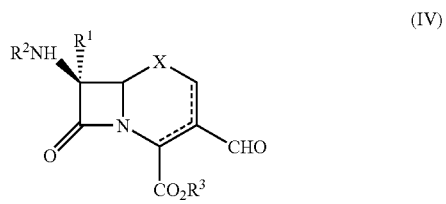
(IV)

with a compound of formula (V):

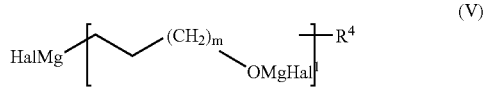
(V)

where $R^1$, $R^2$, $R^3$, X, $R^4$ and m are as defined with respect to formula (III), and Hal and $Hal^1$ are the same or different halogen, and the dotted line in formula (IV) indicates a double bond C2 and C3 or between C3 and C4 of formula IV.

11. A process according to claim 1 or 2, wherein the compound of formula (III) is prepared from a compound of formula (VIII):

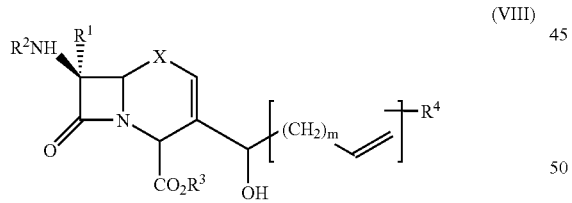
(VIII)

by hydroxylating the compound of formula (VIII) to form the compound of formula (III).

12. A process according to claim 11 wherein the compound of formula (VIII) has hydroxyl group configuration (VIII A):

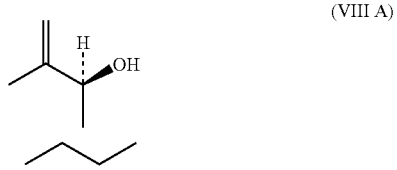
(VIII A)

-continued

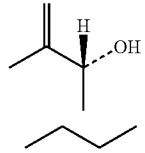
(VIII B)

13. A process according to claim 12 wherein the compound of formula (IV) is formed into a compound of formula (VIII) by reaction with an organometallic reagent.

14. A process according to claim 13 wherein the organometallic reagent is a compound of formula (IX):

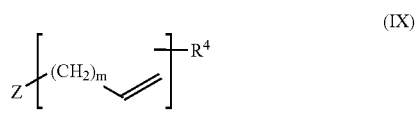
(IX)

where m and $R^4$ are as defined in formula (VIII), and Z is YMg where Y is a halogen.

15. A process according to claim 12 wherein the compound of formula (VIII) is prepared stereospecifically from a compound of formula (IV) by the use of a compound (IX):

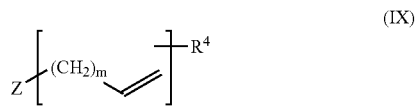
(IX)

in which Z is a chirally inducing group which leads to preferential formation of a desired configuration of the hydroxyl group in the compound (VIII).

16. A process according to claim 15 wherein Z is the boronate group (X):

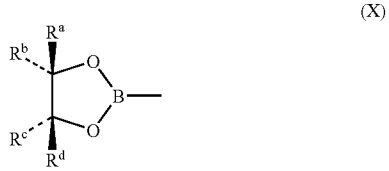
(X)

where $R^a$, $R^b$, $R^c$, and $R^d$ are independently selected from hydrogen, alkyl and protected carboxy.

17. A process according to claim 16 wherein group (X) is a boronate group wherein $R^a$ is alkylcarboxylate, $R^b$ is hydrogen, $R^c$ is alkylcarboxylate and $R^d$ is hydrogen.

18. A process according to claim 10 wherein the compound (IV) is alkylated with a compound of formula V to form a compound of formula VIII, which is then hydroxylated to form a compound of formula (III A):

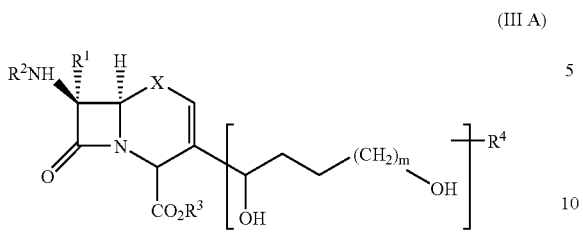
(III A)

which is then cyclized to form a compound of formula (II B):

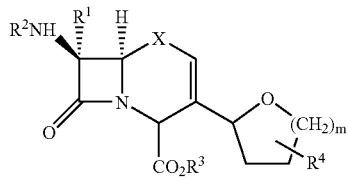
(II B)

where $R^1$, $R^2$, $R^3$, $R^4$, X and m are as defined in formulae (II) and (III) above, and the compound of formula (IIB) is then converted into a compound of the formula (II A)

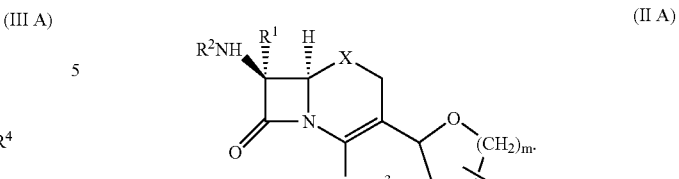
(II A)

19. The process according to claim 1 where $R^3$ is benzyl, p-methoxybenzyl, benzoylmethyl, p-nitrobenzyl, 4-pyridylmethyl, 222, trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, or an oxime radical of formula $-N=CHR^7$ where $R^7$ is aryl or heterocyclic.

20. The process according to claim 1 where $R^3$ is acetoxymethyl, pivaloyloxymethyl, α-acetoxyethyl, α-pivaloyloxyethyl, 1-(cyclohexylcarbonyloxy)prop-1-yl, (1-aminoethyl)carbonyloxymethyl, ethoxycarbonuloxymethyl, α-ethoxycarbonyloxyethyl, propoxycarbonyloxyethyl, dimethylaminomethyl, dimethylaminoethyl, diethylaminomethyl, diethylaminoethyl, 2-(isobutoxycarbonyl)pent-2-enyl, 2-(ethoxycarbonyl)but-2-enyl, phthalidyl, and dimethoxyphthalidyl.

* * * * *